US007348169B1

(12) United States Patent
Singh et al.

(10) Patent No.: US 7,348,169 B1
(45) Date of Patent: Mar. 25, 2008

(54) METHOD OF MAKING BIOACTIVE CATALYTIC MATERIAL

(75) Inventors: Alok Singh, Springfield, VA (US); Yongwoo Lee, Alexandria, VA (US); Evan Stanish, Alexandria, VA (US); Eddie Chang, Silver Spring, MD (US); Walter J. Dressick, Fort Washington, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 37 days.

(21) Appl. No.: 11/434,579

(22) Filed: May 4, 2006

Related U.S. Application Data

(62) Division of application No. 10/750,637, filed on Dec. 23, 2003, now Pat. No. 7,067,294.

(51) Int. Cl.
*C12N 9/00* (2006.01)

(52) U.S. Cl. ........................ 435/183; 435/18; 435/175

(58) Field of Classification Search ................ 435/183, 435/18, 174, 175, 195; 424/491
See application file for complete search history.

(56) References Cited

U.S. PATENT DOCUMENTS 6,869,784 B2 * 3/2005 Singh et al. ................ 435/188
7,067,294 B2 * 6/2006 Singh et al. ................ 435/174

OTHER PUBLICATIONS

Lee, Y. et al. Sustained Enzyme Activity of Organophosphorus Hydrolase in Polymer Encased Multilayer Assemblies. Langmuir vol. 19, 1330-1336, 2003.*

* cited by examiner

*Primary Examiner*—Ralph Gitomer
(74) *Attorney, Agent, or Firm*—Stephen T. Hunnius; John J. Karasek

(57) ABSTRACT

A bioactive catalytic material is disclosed for providing protection from chemical exposure. The material is composed of enzymes immobilized within polyelectrolyte multilayers and a polymerizable end-capping layer to render stability to enzymes. Also disclosed is the related method for making a bioactive catalytic material and their deposition on substrates of varying size, shape and flexibility for providing active protection from chemical exposure.

18 Claims, 8 Drawing Sheets

METHOD OF MAKING BIOACTIVE CATALYTIC MATERIAL

This application is a divisional application of U.S. application Ser. No. 10/750,637 filed on Dec. 23, 2003 now U.S. Pat. No. 7,067,294, incorporated herein by reference.

BACKGROUND

1. Field of the Invention

The present invention relates to catalytic surfaces, and, more specifically, to catalytic surfaces for active protection from air or water borne toxins by passivation and adsorption of toxic materials.

2. Description of the Prior Art

There is an urgent need for the development of effective means to protect people and the environment from the exposures of toxic chemicals and other threat agents irrespective of the cause of exposure, accidental or due to terrorist act. Moreover, there is a need to protect against prolonged exposure to small amounts of toxic chemicals (such as pesticides), since persistent encounters with small quantities of toxic chemicals, especially in a closed environment, may be more dangerous than a one-time encounter with a larger quantity. The existing technologies use barrier protection to protect people and the environment involving materials of high absorbing capacity. The most widely used adsorbent is active charcoal, which leads to the development of bulky materials. Materials used in barrier protection are bulky and have only one useful life cycle. While the barrier technologies provide adequate protection, they have the serious technical problem of disposal of the materials at the end of their active life cycle because of the presence of toxic materials in concentrated form. Other concerns include weight, capacity and inconvenience during practical use.

Another existing technology regarding toxic chemicals is the use of enzymes. Enzymes are the most effective catalyst against chemical agents but have limited long-term stability. Also, they lose their catalytic activity during immobilization steps. See G. F. Drevon, K. Danielmeier, W. Federspiel, D. B. Stolz, D. A. Wicks, P. C. Yu & A. J. Russell, "High-activity enzyme-polyurethane coatings," Biotechnology and Bioengineering, 79 (7): 785-794, 2002 and G. F. Drevon & A. J. Russell, "Irreversible immobilization of diisopropylfluorophosphtase in polyurethane polymers, Biomacromolecules, 1 (4): 571-576 (2000), both of which are incorporated herein by reference. Lack of stability and loss of catalytic activity render enzymes unsuitable for protection applications. Several techniques have been reported for stabilizing the enzymes—most of them focusing on their immobilization to a suitable substrate. However, chemical linking to the surface causes the enzymes to lose their activity substantially. Non-covalent immobilization of enzymes on vesicles provides an effective means to retain enzyme activity. See U.S. Pat. No. 5,663,387 to Singh, incorporated herein by reference. Deposition of a single layer of enzymes on a surface is good for a sensor application, but not adequate for chemical agent passivation applications, which require a larger amount of enzymes to effectively hydrolyze the toxic chemicals.

SUMMARY

The aforementioned problems are overcome by the present invention wherein a bioactive catalytic material for providing protection from chemical exposure that is stable and retains its catalytic activity comprises at least one enzyme immobilized within at least one polyelectrolyte and a polymerized end-capping layer. The present invention provides novel, bioactive, catalytic materials for providing protection against chemical agents, which are more effective than barrier protection. These catalytic materials can be in the form of clothing (e.g. gloves, shoes, shirts, pants, etc.), filters, (e.g. masks, sponges, air-vent cartridges, etc.) and aerosols or suspensions (e.g. sprays to coat electronic devices, lotions, etc.). All of these examples serve as potential physical supports on which to coat the proposed technology, which is based on microscopic layering principles.

In a preferred embodiment, the present invention takes advantage of superior catalytic activity of enzymes by immobilizing them within polyelectrolyte multilayers. The technique for forming multilayers is simple and effective as polyelectrolytes of opposing polarity are alternatively deposited through neutralization and overcompensation of their charges. See G. Decher, "Fuzzy nanoassemblies: Toward layered polymeric multicomposites," Science, 277, 1232-1237, 1997, incorporated herein by reference. Enzymes immobilized in the multilayers are easily accessible to the incoming toxic materials and, thus, passivate them efficiently. An end-capping agent is anchored to the outermost layer and then polymerized. The end-capping agent provides stability to the multilayers, keeps enzymes protected in adverse working environments, and attracts the toxic agents to facilitate contact with the catalytic sites.

The present invention provides several advantages over the prior art. It leads to enhanced enzyme shelf life under normal storage conditions. It allows incorporation of multiple components into multilayers to provide add-on capabilities to the packaged system. It is lightweight, robust sturdy, disposable, self-decontaminating, and cost-effective. It offers versatility as it can be designed for uses in various forms and in different places depending on the need.

BRIEF DESCRIPTION OF THE DRAWINGS

These and other objects, features and advantages of the invention, as well as the invention itself, will become better understood by reference to the following detailed description, appended claims, and accompanying drawings where:

DETAILED DESCRIPTION

Figure 1:
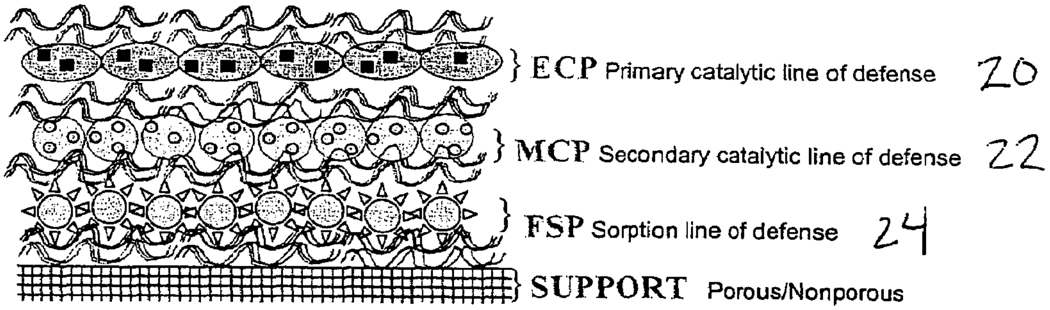
FIG. 1 shows bioactive system prototype 1, which is composed of a tri-layer assembly consisting of enzyme-coated particles (ECP), metal-chelating particles (MCP), and functionalized silica particles (FSP) placed on a support that can be either porous or non-porous.

The core of the present invention is the packaging of essential components within alternate layers, or within a single layer, to produce bioactive thin film and the stabilization of catalytic components and multilayer assemblies to make them durable without losing their performance. Catalysts are immobilized within polyelectrolytes to degrade chemical agents and selectively capture degradation products. An end-capping layer provides structural robustness and resists aggressive physical and chemical perturbations.

In a preferred embodiment, the catalysts include enzymes, classless non-specific catalysts, and adsorbent particles. Preferred enzymes are those that are superior catalysts for degrading chemical agents with high turnover numbers. Based on the need and application, any commercially available enzyme can be used. Examples of preferred enzymes include organophosphorous hydrolase (OPH), organophosphorous acid anhydrolase (OPAA), DFPase, phosphotriesterases (PTE), and combinations of enzymes capable of passivating a large number of toxic agents. A combination of OPH or PTE with OPAA will destroy most of the chemical agents used in warfare.

Classless non-specific catalysts catalyze hydrolysis of chemical agents at a slower rate than enzymes. Examples of preferred classless non-specific catalysts include metal chelated catalytic particles (MCCP) such as metal chelated (EDA-$Cu^{2+}$) polymers, silica particles, and $TiO_2$. $TiO_2$ particles are useful for light induced degradation of chemical and biological agents because they have appropriate oxidizing or reducing power during illumination due to their band gap so as to decompose target particles. MCP are useful in degrading those chemical agents that are not degraded by enzymes.

Adsorbent particles are functional catalytic particles (FCP) made by incorporating quaternary ammonium surfactant to silica microparticles. Also, acidic or basic alumina may be used to capture degradation products and biological particles. FCP partially hydrolyze chemical agents and selectively capture degradation products.

A chemically functionalized material is used as a support for the catalytic components. Examples of supports include glass beads of various diameters, microporous surfaces, electrospun fibers containing surface available chemically active functionalities, fabric from glass, synthetic fibers (e.g. nylon), natural fibers (e.g., cotton, wool), and polymer films. The catalytic components coated on a support can take many forms, including clothing, filters, aerosols, and suspensions.

A molecular "glue" is used to hold all the active catalytic components together, to stabilize enzymes, and to provide adequate adhesion of the assemblies to the support materials without involving any chemical reaction. Polyelectrolytes, by virtue of available cationic or anionic functionalities in abundance, provide an excellent means to glue the molecular components. Cooperativity and electrostatic interactions such as hydrogen bonding and Van der Waals between anionic and cationic sites leads to the formation of strong association of multilayers. Examples of polyelectrolytes that can be used include commercially available polyelectrolytes, branched or linear polyethyleneimine (PEI), polyacrylic acid (PAA), polystyrene sulfonate (PSS), polydiallyl dimethyl ammonium chloride (PDDA), polyvinylpyridine (PVP), polyvinyl sulfate (PVS), polyallyl amine hydrochloride (PAR) and their chemically altered derivatives.

An end-capping agent is used to encase the catalytic components. The end-capping agent provides stability to the catalytic components, keeps the enzyme architecture dimensionally protected in adverse working environments, and ideally attracts the toxic agents to facilitate contact with the catalytic sites. In a preferred embodiment, pH- and photopolymerizable monomers, metal-ion crosslinked systems are used as end-capping agents. In an even more preferred embodiment, the end-capping agent is selected from the group consisting of 1,2-dihydroxypropyl methacrylate (DHPM), 1,2-dihydroxypropyl 4-vinylbenzyl ether (DHPVB), and N-[3-(trimethoxysilyl)propyl]ethylenediamine (TMSED). Preferably, polyamine silane derivatives, in addition to endcapping agents cross-linkable polyelectrolytes can be used.

Figure 2:
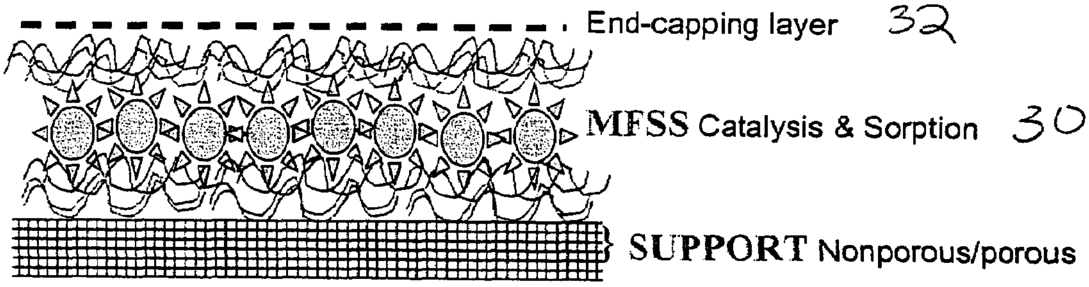
FIG. 2 shows bioactive system prototype 2, which is composed of multifunctional solid supports (MFSS) that serve the dual purpose of catalyzing toxins and concomitantly sorbing its by-products and a top-layer molecular sheet to protect and stabilize the single layer assembly.

In a preferred embodiment as shown in FIG. 1., a multifunctional tri-layer assembly is composed in series of enzyme-coated catalytic particles (ECP) (20) as the primary line of catalysis, metal-chelated catalytic particles (MCCP) (22) as the secondary line of catalysis, and functionalized catalytic particles (FCP) (24) as the final line of protection which will adsorb residual non-catalyzed toxins and its by-products. In another preferred embodiment as shown in FIG. 2, a more advanced system combines the functions of both catalysis and sorption in a single layered system. The layer-by-layer technique is exploited to immobilize multifunctional solid supports (MFSS) (30) and to provide the primer for a stabilizing outer end-capping layer (32). The system illustrated in FIG. 2 is not limited to catalysis by enzyme immobilization. Multiple enzymes with varying substrate specificity can be immobilized to expand the detoxifying scope of this system. The potential types of enzymes individually or as mixture incorporated in the system are not bound by any limit. Enzymes that have been studied include OPH, OPAA, phosphotriesterase (PTE), glucose oxidase (GOD), and alkaline phosphatase (AP).

EXAMPLE 1

Multilayer Formation and Assembly Stabilization

Figure 3A:
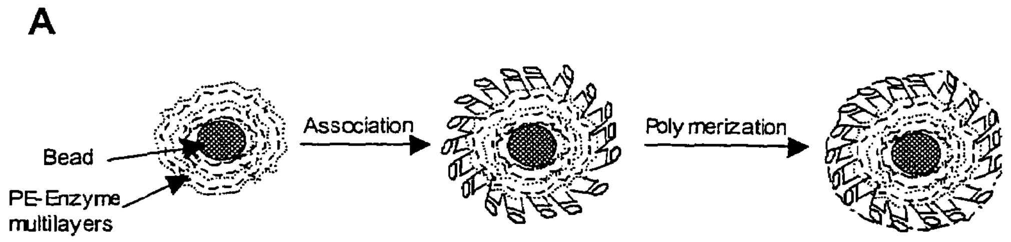
FIG. 3*a* is a schematic representation of multilayer stability via an outer-layer polymer net on enzyme-polyelectrolyte multilayers.
Figure 3B:
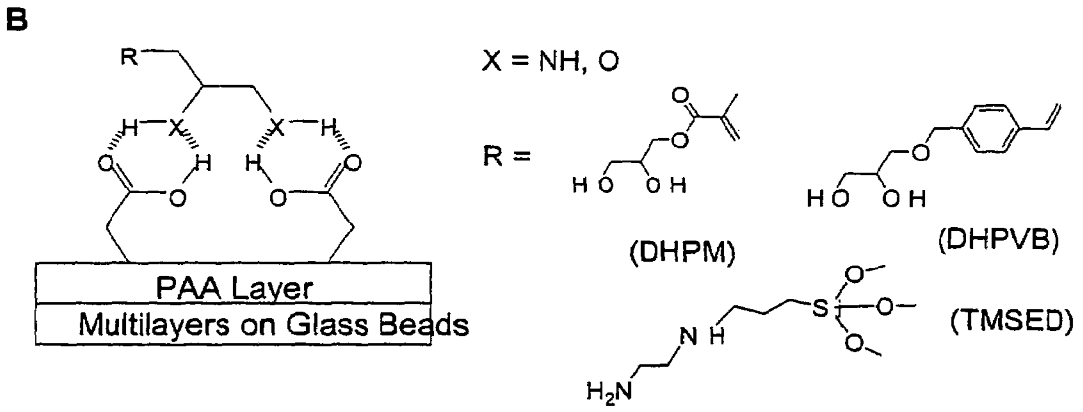
FIG. 3*b* shows the hydrogen bonding association between a polyacrylic acid layer and the end-capping monomer in multilayer stabilization via an outer-layer polymer net (BPEI is branched-polyethyleneimine, PAA is polyacrylic acid, PSS is polystyrene sulfonate, PDDA is polydiallyl dimethyl ammonium chloride)

As illustrated in FIGS. 3*a* and 3*b*, polyelectrolyte multilayers were formed on glass beads (30-50μ) by sequential immersion in their respective polyelectrolyte solution. Polyelectrolytes were dissolved in water and their pH was adjusted by adding dilute solution of hydrochloric acid or sodium hydroxide. After treatment with each polyelectrolyte solution (1-5 mM) (preferably 10 minutes), the substrates were briefly washed with deionized water, and the supernatant was decanted to remove the extraneous polyelectrolyte adhered to the surface. Both glass beads and gold resonators were first modified by putting down an initial branched polyethyleneimine (BPEI) layer followed by deposition of three alternating layers of PSS-BPEI to make a BPEI-(PSS-BPEI)$_3$-assembly to serve as precursor layers. Gold resonator were used for quantitative determination of mass of the deposited layers and the enzymes. The gold resonators are made from quartz on which gold film is coated in a predefined circle—when the layer is deposited on the gold the vibration of quartz is impeded, which were directly related to the change in mass on the resonator. Then, five alternating enzyme-polyelectrolyte layers were deposited. For glass beads, the final configurations were silica-(BPEI-PSS)$_3$-(BPEI-enzyme)$_5$ and silica-(BPEI-PSS)$_3$-(BPEI-enzyme)$_5$-PAA. Upon completion, the OPH multilayered beads were freeze-dried and stored in a desiccator at room temperature.

Beads containing PAA as an outermost layer were treated with 10 mL aliquot of end-capping monomers (concentration ranging from 0.5-1.5 mM) in a centrifuge tube mounted on a Laboratory Rotator® at 35 rpm for 10 minutes and rinsed with water. Water was removed from the beads by freeze-drying. Glass beads had the following multilayer configuration: silica-BPEI-PSS)$_3$-(BPEI-OPH)$_5$-PEI-PAA-endcapping monomer. Polymerization of monomers deposited on gold resonators and glass beads was carried out by photopolymerization or by raising solution pH. Glass beads having the outer DHPVB monomer layer were mixed and photopolymerized (254 nm for 3 minutes) in a UV reactor at room temperature. Glass beads having the outer TMSED monomer layer were polymerized by immersing them in 0.15% $NH_4OH$ solution with gentle agitation (30 seconds).

EXAMPLE 2

Deposition of OPH on Woven Glass Cloths

Polyelectrolyte multilayers were formed on glass cloth and cotton cloth in a similar manner as for glass beads. The glass (or silica) cloth used was from Hexcel Schwebel—STYLE 106 with a fabric weight of 25 g/m$^2$, plain weave style, warp count 56, fill count 56, 0.04 mm fabric thickness, and 45 lbf/in breaking strength; however, any glass cloth can be used. The sequence of multilayer deposition was silica-BPEI/water-OPH/BTP-BPEI/BTP. The preferred deposition method consisted of dipping the cloth in a polyelectrolyte solution. The RCA Procedure was used for cleaning [MeOH: HCl, 1:1, (2 hours); water rinse; 95% $H_2SO_4$ (30 min), water rinse]. The following procedure was used for deposition: 3 mM BPEI/H2O (8.6) 10 min.; wash with $H_2O$ 10 min, OPH-10 mM BTP (8.6) 10 min.; wash with BTP (8.6) 1 min; BPEI/BTP (8.6) 10 min.; BTP 1 min; PSS (6.6) 10 min.; repeat the sequence for more layers. Excess water was removed by snapping the cloth followed by drying in vacuum at least for two hours. The cloths were stored in a refrigerator. The protocol for measuring the catalytic activity in bulk (batch reactor) was as follows: place cloth in 100 mL, 100 μM MPT solution (20% MeOH in water) stir for 22 hours at room temperature; withdraw 600 μL aliquot and analyze for PNP produced. After each cycle fresh solution of MPT was used. Silica cloth in a batch reactor showed 18% hydrolysis of MPT in each cycle. Hydrolysis capacity of the cloth was maintained for 19 days. Sustainment of 50% hydrolytic capacity was monitored in the second and third week of reuse of the silica cloth.

EXAMPLE 3

Deposition of OPH on Cotton Cloths

For cotton cloth, a commercial cotton fabric was used. The sequence of multilayer deposition was silica-BPEI/water-OPH/BTP-BPEI/BTP, and an identical method for the multilayer deposition was used. The catalytic activity was measured in the same way as described for glass cloth. While, cotton cloth also retained its activity after reusing it for three weeks (while storing the cloth in refrigerator for the week-end), it showed a three times higher activity than observed for glass cloth.

EXAMPLE 4

Activity of Enzymes in Multilayers

Figure 4:
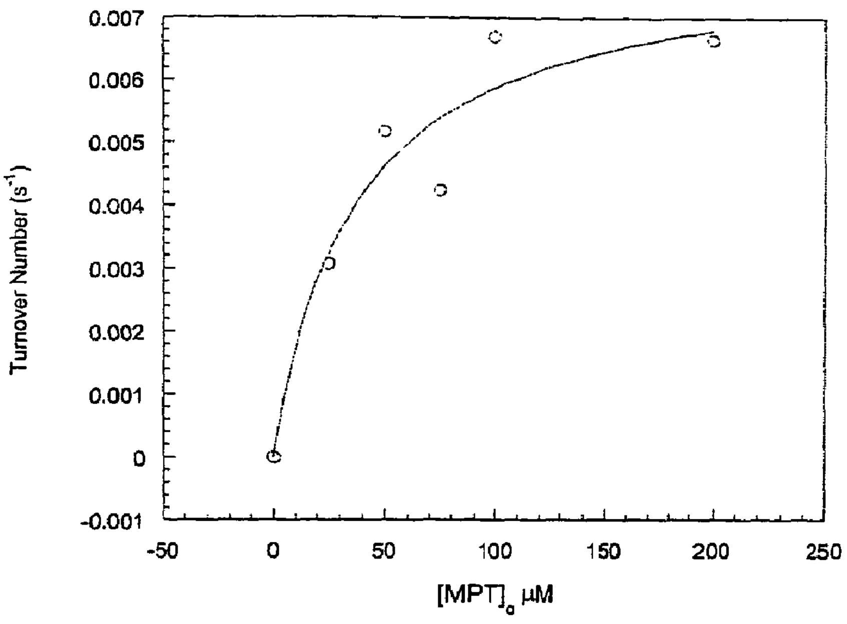
FIG. 4 shows the organophosphorous hydrolase (OPH) turnover rate as a function of initial methyl parathion (MPT) concentration at pH 8.6 in 10 mM CHES buffer and 15% v/v methanol; layers of OPH are deposited on silica spheres (30-50 μm): Silica-$(BPEI\text{-}PSS)_3$-$(BPEI\text{-}OPH)_5$-PEI.

OPH hydrolyzes methyl parathion (MPT) to produce para-nitrophenol (PNP) and dimethoxyphosphinothioxo-1-ol. PNP has a strong extinction coefficient and therefore allows for easy spectrophotometric monitoring of MPT hydrolysis. As shown in FIG. 4, OPH catalysis is linear (i.e., first order) at low MPT concentration (<27 μM) and plateaus at higher MPT concentrations to an apparent maximum turnover rate of 0.01 $s^{-1}$. In the present invention, substrate diffusion within the multilayers and enzyme accessibility are two phenomena affecting the rate of MPT hydrolysis. The rate of catalysis measured for the present invention is comparable with those observed for free OPH in solution. Polymer net coatings provide minimal resistance or at least are not rate limiting since only a molecular sheet is used to encase and protect the multilayer assembly. The performance of the OPH-multilayer beads was investigated for the degradation of diisopropyl fluorophosphate (DFP), a nerve agent simulant, and the turnover rate for OPH hydrolysis was 15.38 $s^{-1}$. As in the hydrolysis for MPT, OPH hydrolysis of DFP lags with respect to the kinetic parameters obtained for the free enzyme. This is reasoned with the same arguments presented above. One should note that the rate of hydrolysis for these toxic agents using the present invention is extremely rapid relative to chemical treatments and does not leave undesirable by-products nor is it corrosive to the environment.

Figure 5:
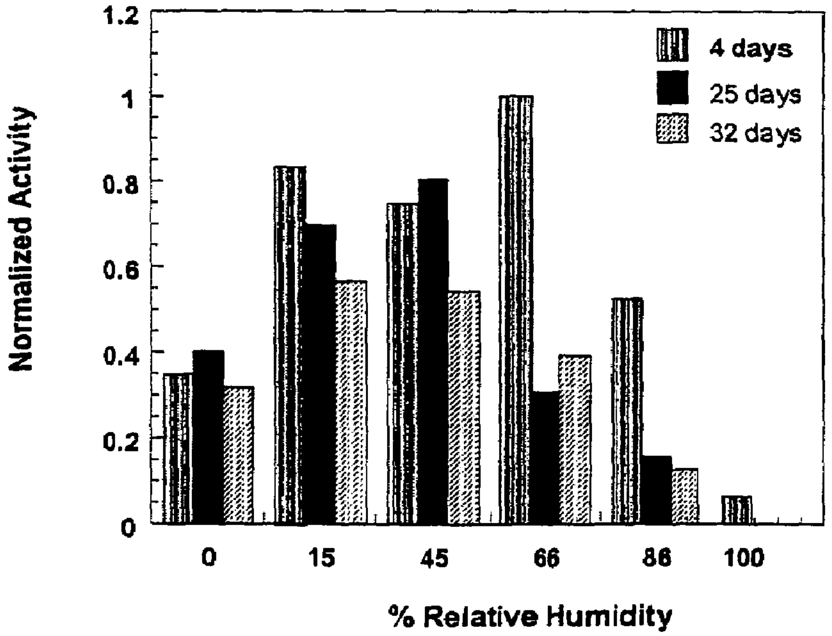
FIG. 5 shows organophosphorous hydrolase (OPH) activity against methyl parathion (MPT) as a function of relative humidity over time; Silica-(BPEI-PSS)$_3$-(BPEI-OPH)$_5$-PEI.

OPH multilayer assemblies on glass beads were evaluated for their activity as a function of humidity (0-100% relative humidity) and as a function of time at room temperature and atmospheric pressure. As shown in FIG. 5, a skewed bell-shape curve arose from normalized activity (relative to the most active system) plotted against humidity. Higher enzyme activity was observed under dry conditions relative to that of the liquid state and unexpectedly peaks near 66% relative humidity. Enzyme activity in multilayer assemblies increased with increasing relative humidity up to 66%, but decreased more rapidly beyond this level of wetness. As expected, enzyme activity decayed with time. In aqueous media, enzyme activity decayed rapidly (i.e., within a few days). However, under dry storage conditions, the enzyme remained active over a period of several months.

Figure 6:
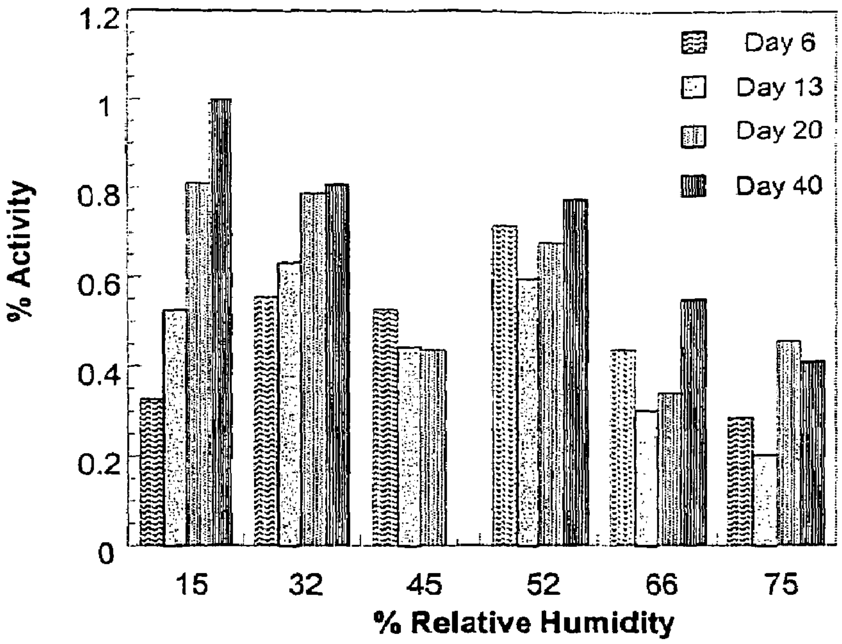
FIG. 6 shows glucose oxidase (GOD) activity against glucose as a function of relative humidity over time; Silica-(BPEI-PSS)$_3$-(BPEI-GOD)$_5$.

GOD multilayer assemblies on glass beads were evaluated for their activity after subjecting them to varying humidity environment (0-100% relative humidity) and as a function of time at room temperature and pressure. As shown in FIG. 6, a bell-shape curve arose from normalized activity (relative to the most active system) plotted against relative humidity, peaking near 52%. Higher enzyme activity was observed over time, which may indicate optimum reorientation of the enzyme within the multilayers. Enzyme activity in multilayer assemblies increased with time. After 40 days of storage, enzyme activity displayed a somewhat downward linear response with increasing humidity. As with OPH, GOD also decayed rapidly in aqueous media (i.e., 100% relative humidity), but can remain active over several months under dry storage conditions.

EXAMPLE 5

Stability

Figure 7:
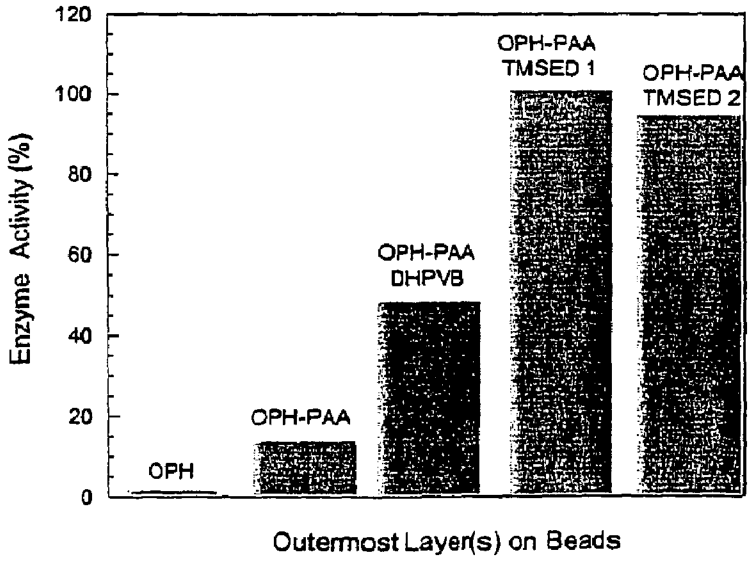
FIG. 7 shows the percent activity against salt stress of non-capped organophosphorous hydrolase (OPH) multilayer beads, PAA capped multi-layer OPH beads, polymerized 1,2-dihydroxypropyl 4-vinylbenzyl ether (DHPVB) on polyacrylic acid (PAA) end capped multi-layer OPH beads, polymerized N-[3-(trimethoxysilyl)propyl]ethylenediamine (TMSED) on PAA capped multi-layer OPH beads, and mildly polymerized TMSED on PAA capped multi-layer OPH beads.

DHPVB and TMSED end-capped multilayer assemblies on glass beads were obtained by sequential adsorption of PAA and end-capping monomers on OPH terminated multilayer assemblies. Activity of polymer encased enzyme-multilayers was determined immediately after their formation and compared with the activity observed for the beads after subjecting them to stress, using sodium chloride solutions. Beads obtained after constructing a polymer net involving polymerized DHPVB or TMSED showed enzyme activity comparable to beads without a polymer net. FIG. 7 shows the percent of enzyme activity against salt stress of non-capped OPH multilayer beads, PAA capped multi-layer OPH beads, polymerized VB on PAA end-capped multi-layer OPH beads, polymerized TMSED on PAA capped multi-layer OPH beads, and mildly polymerized TMSED on PAA capped multi-layer OPH beads. Initial activity of $1.8\times10^{-9}$ M/s observed for OPH coated glass beads was completely lost upon their exposure to 2M NaCl solution (2 h). Under the same salt stress condition, OPH in multilayers coated with a PAA layer showed minimal activity (3% of maxinum activity). DHPVB end-capped OPH coated glass beads were more active showing 12% retention of original activity. TMSED coated OPH glass beads, having 27% relative activity, were the most effective against salt stress.

EXAMPLE 6

BioSorption Systems

Figure 8:
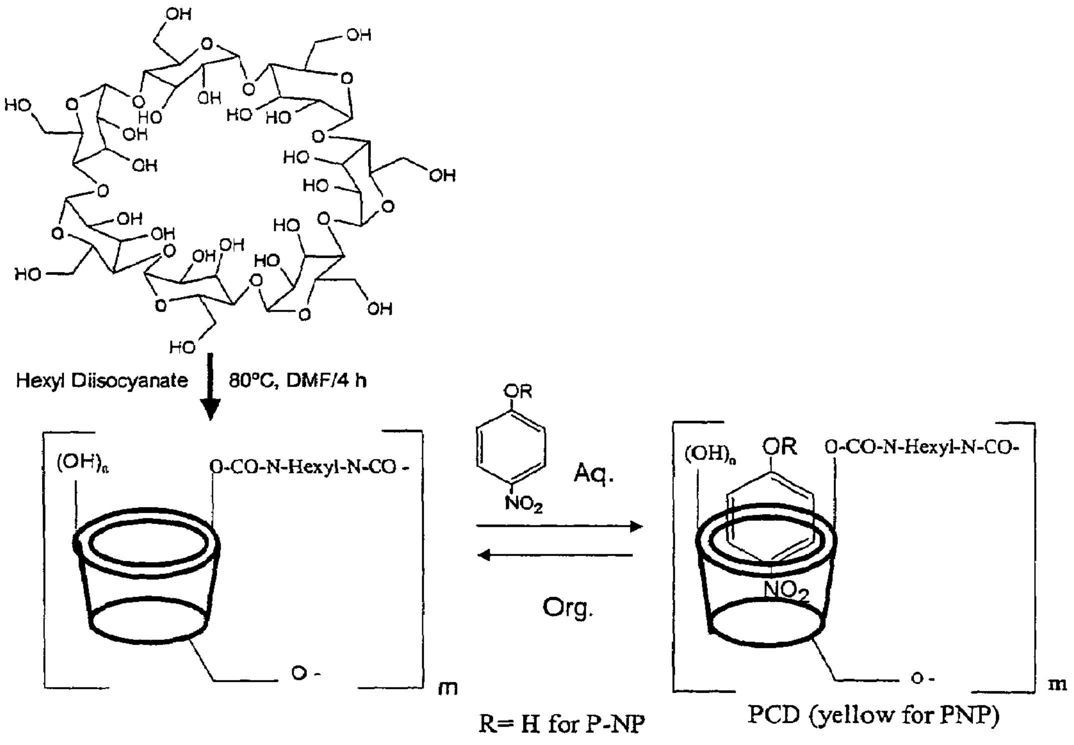
FIG. 8 shows poly-β-cyclodextrins (PCD) prepared by crosslinking (β-cyclodextrins with alkyl diisocyanates to support multilayer assemblies and absorb hydrolysis products.
Figures 9A, 9B, 9C, 9D:
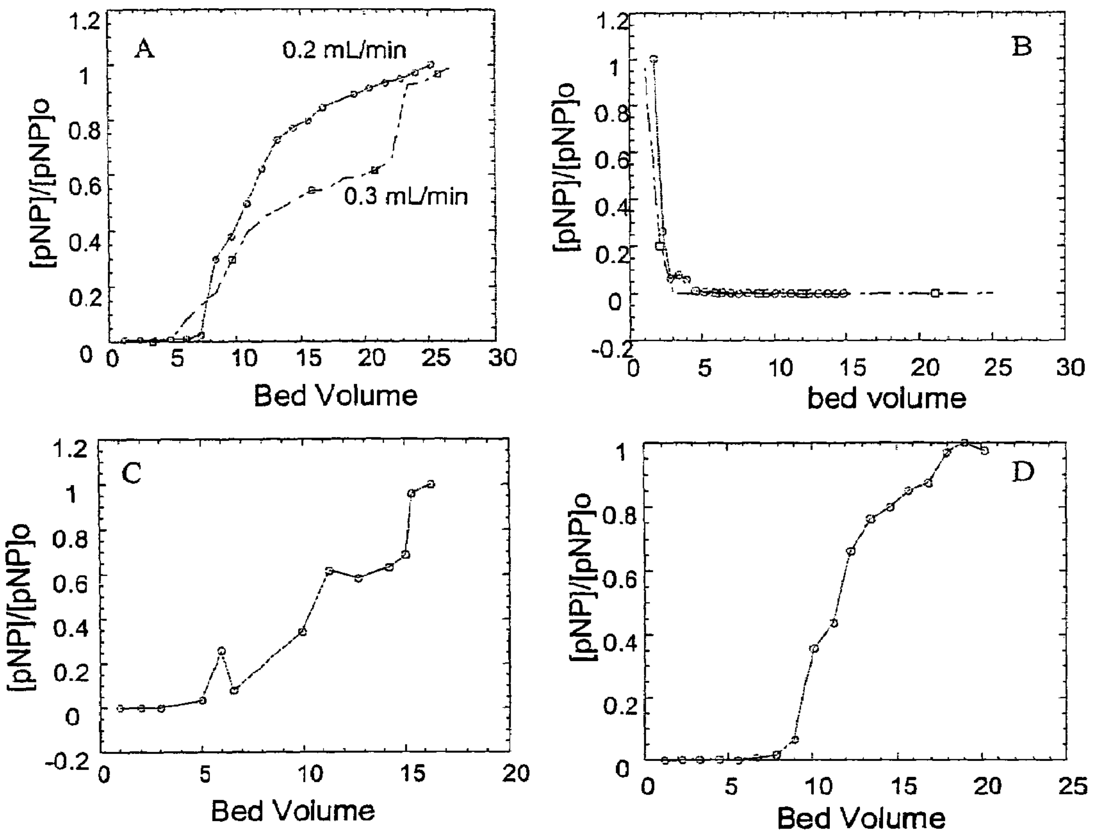
FIG. 9*a* shows a breakthrough curve using PCD (30-50 μm) for para-nitrophenol (pNP) (1 mM, pH 8.6) sorption at two different flow rates (0.2 mL/min and 0.3 mL/min)
FIG. 9*b* shows a regeneration of PCD within two columns provided in FIG. 9*a* using ethanol (0.2 ml/min)
FIG. 9*c* shows a breakthrough curve for para-nitrophenol (PNP) (1 mM, pH 1) sorption by PCD at low pH.
FIG. 9*d* shows a breakthrough curve for methyl parathion (MPT) (0.1 mM, pH 8.6, 15% v/v methanol) sorption by PCD.

Crosslinked poly-β-cyclodextrin (PCD) were synthesized and evaluated for its PNP (a by-product of MPT) sorbing properties. FIG. 8 is the schematic representation of the PCD. FIG. 9*a* shows the sorption behavior of PCD for PNP with increasing flow rate. At a slower flow rate (0.2 mL/min), a steep break-through was observed to occur at 7 bed volumes. At a higher flow rate (0.6 mL/min), break-through occurred near 5 bed volumes and was less steep tailing off at 25 bed volumes. Output feed was normalized to the input PNP feed (1 mM, pH 8.6). After the completion of the experiment, these PNP loaded PCD columns were regenerated in pure ethanol (see FIG. 9*b*). Recovery of PNP from these packed columns was complete after 3 bed volumes. This signifies that a chemical toxin such as pNP can be sorbed from relatively dilute solution and then regenerated in concentrated form for possible resale. The effect of pH was investigated for this system. At pH 1, PCD sorption increased relative to pH 8.6. FIG. 9*c* illustrates improved breakthrough performance at pH 1 (0.2 mL/min). Breakthrough occurred at a higher bed volume (i.e., 10) and with a steeper breakthrough slope. Sorption of MPT by PCD was also demonstrated by this system (see FIG. 9*d*). MPT feed concentration was ten times less (i.e., 0.1 mM in the presence of 15% v/v methanol). Breakthrough occurred near 7 bed volumes, similar to PNP sorption but less sharp. Note that mass, volume, and flow rate were held constant.

EXAMPLE 7

Combined BioCatalysis/Sorption System

Figure 10:
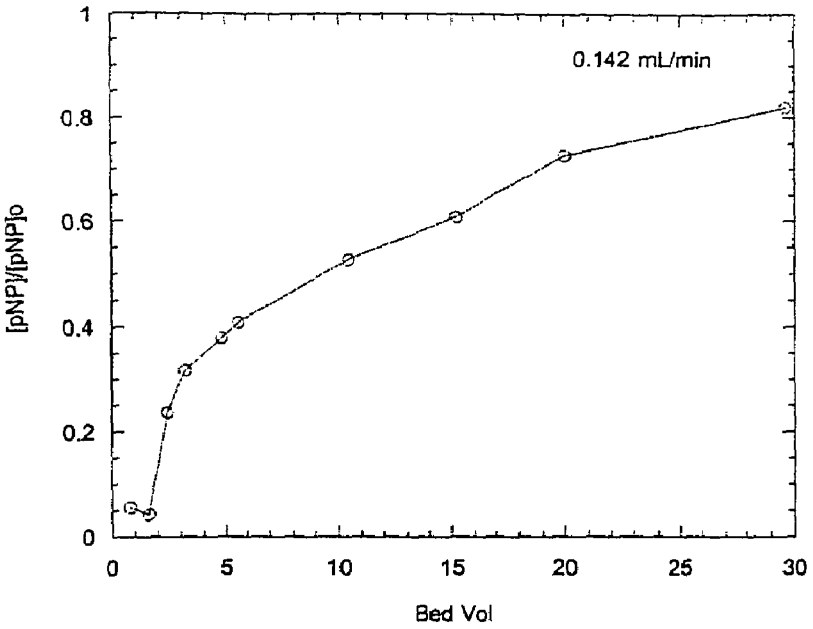
FIG. 10 shows catalytic and sorption behavior of PCD for methyl parathion (MPT) (0.1 mM, pH 8.6, 15% v/v methanol)

Crosslinked poly-β-cyclodextrin (PCD) was evaluated for its catalytic and sorption behavior for MPT. FIG. 10 shows the complete removal of MPT or PNP in the first few bed volumes. It is also clear from the yellow color (expected from PNP) of the packed column that PCD is acting as a catalyst for MPT hydrolysis. FIG. 10 shows that after 30 bed volumes, the system saturates and neither catalysis nor sorption remains active.

EXAMPLE 8

Fabrication of Catalytic Films for Making Masks and Lightweight Protective Clothing Multilayers involving OPH, polyelectrolytes (BPEI, PAA), and end-capping agent TMSED were deposited on Low E-glass cloth. The successful deposition following the techniques described earlier shows the versatility of the process. The catalytic layers on glass cloth were found to be very active against MPT. Wiping the MPT contaminated surface with glass cloths turned the cloth yellow due to the formation of p-nitrophenol upon hydrolysis. Common laboratory protective gloves were also used for deposition of catalytic films after acid treatment of the surface. Acid treatment facilitated the deposition of catalytic multilayers.

EXAMPLE 9

Classless Non-Specific Catalysts for Degradation of Toxic Agents

Cu(II)-containing functionalized monomers of either vbpy (4-vinyl-4'-methyl-2,2'-bipyridine) or [9]ane (e.g. 1,4,7-tris(4-vinyl)benzyl-1,4,7-triazacyclononane of [9]ane$N_3$) were cross-linked to TRIM (trimethylolpropane trimethacrylate) to form insoluble catalytic polymers. Measurement of rates of spontaneous and Cu(II)(bpy) catalyzed hydrolysis of chemical agent simultant p-nitrophenyl phosphate (NPP), bis-(p-nitrophenyl) phosphate (BNPP), and MPT were carried out at 20 to 22° C. in 85:15 water/methanol with 100 mM MOPS ([3-(N-morpholino)propanesulfonic acid] sodium salt) at pH 8.1. TRIM polymers, obtained from the protocol described herein, formed a fine powder with a very high surface area of 406 $m^2/g$. The polymer matrix was also microporous with an average pore diameter of approximately 2.5 nm. While much of the powder was made up of particles greater than 10 μm that settle quickly, dynamic light scattering of the supernatant from sonicated samples shows a bi-modal size distribution of suspended particles with diameters centered about 5.3 and 0.15 μm. Polymeric TRIM based catalyst also showed strong adsorptive affinity towards the chemical agents.

The initial rates of hydrolysis were measured, and $k_{obs}$, the observed pseudo first-order rate constant, and $V_{max}$ and $K_m$, the maximal velocity and the characteristic constant derived from a Michaelis-Menton kinetics model, were calculated. From $V_{max}$, $k_{cat}$, the catalytic rate constant in $s^{-1}$, was obtained. As shown in Table 1, the polymers were $2.2\times10^6$ and $2.3\times10^4$ times more rapid than the uncatalyzed hydrolysis of BNPP and MPT, respectively. In comparison to the soluble chelator-metal systems, the polymer systems were even 16 and 18 times more effective, respectively.

TABLE 1

Hydrolysis Rates as $k_{cat}$

| Substrate | Catalyst/Enzyme | Catalysis Rate ($s^{-1}$) | Ratio $k_{cat}/k_{uncat}$ |
|---|---|---|---|
| BNPP | (uncatalysed)[a] | $1.1 \times 10^{-11}$ | — |
| BNPP | bpy: Cu (aq) | $1.5 \times 10^{-6}$ | $1.3 \times 10^{5}$ |
| BNPP | vbpy polymer: Cu | $2.4 \times 10^{-5}$ | $2.2 \times 10^{6}$ |
| MPT | (uncatalysed)[b] | $8 \times 10^{-7}$ | — |
| MPT | Cu (aq)[b] | $3 \times 10^{-5}$ | 38 |
| MPT | bpy: Cu (aq) | $1.4 \times 10^{-3}$ | $1.7 \times 10^{3}$ |
| MPT | vbpy polymer: Cu | $2.0 \times 10^{-2}$ | $2.5 \times 10^{4}$ |

[a]Takasaki and Chin, J. Am. Chem. Soc., v. 117, 8582-8585 (1995)
[b]Smolen and Stone, Environ. Sci. Technol., v. 31, 1664-1673 (1997)

Figure 11:
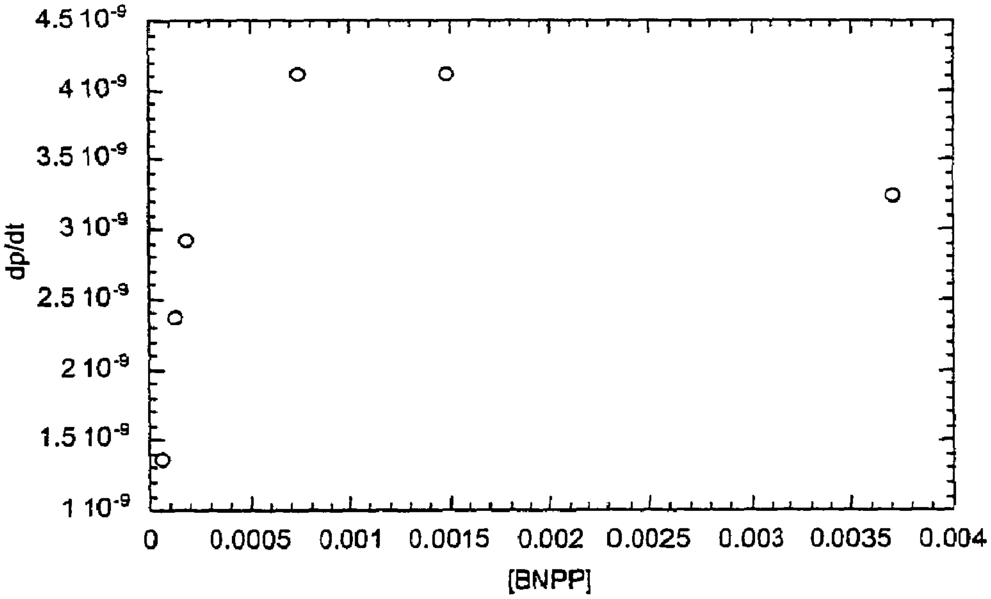
FIG. 11 shows bis-(p-nitrophenyl) phosphate (BNPP) hydrolysis with metal chelated polymer catalyst.

The strong adsorptive power of the polymeric TRIM catalysts for the substrates is evident as, above a certain substrate concentration, the rate of reaction will actually decrease somewhat through a well-known "substrate inhibition" mechanism. Thus, FIG. 11 shows the rate increasing then slowly decreasing with increasing initial substrate concentrations.

Figure 12:
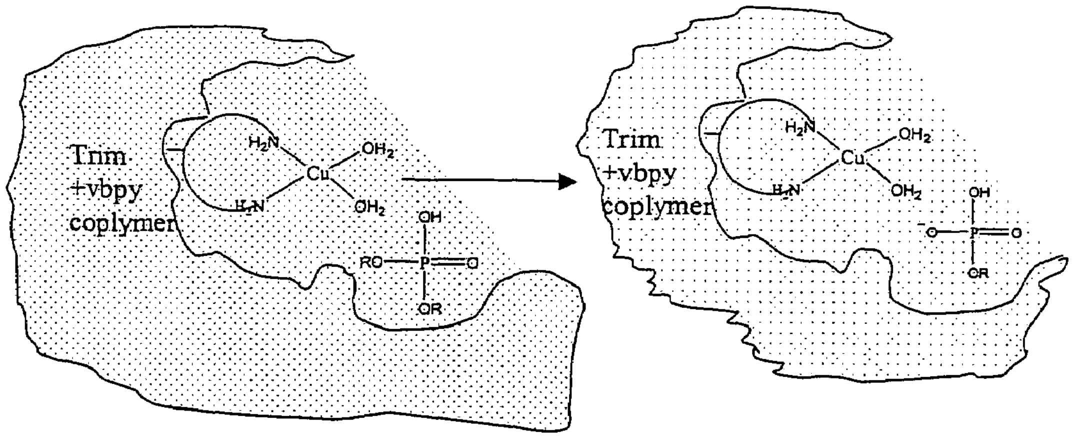
FIG. 12 shows hydrolysis of phosphate esters by metal chelated catalytic polymer made by crosslinking of trimethylolpropane trimethacrylate (TRIM) and vinylbenzenyl diamine precursors.

As shown in FIG. 12, chelated polymer catalytic particles were made with [9] ane $N_3$, that is functionalized with three vinylbenzene groups through the cyclononane nitrogens. This strong adsorption of substrate is a desirable property for prevention of any substrate leakage through the filters.

The above description is that of a preferred embodiment of the invention. Various modifications and variations are possible in light of the above teachings. It is therefore to be understood that, within the scope of the appended claims, the invention may be practiced otherwise than as specifically described. Any reference to claim elements in the singular, e.g. using the articles "a," "an," "the," or "said" is not construed as limiting the element to the singular.

The invention claimed is:

1. A method of making a bioactive catalytic material comprising the steps of:
- (a) immobilizing at least one enzyme within at least one polyelectrolyte;
- (b) depositing an end-capping agent selected from the group consisting of 1,2-dihydroxypropyl methacrylate (DHPM), 1,2-dihydroxypropyl 4-vinylbenzyl ether (DHPVB), N-[3-trimethoxysilyl)propyl]ethylenediamine (TMSED), and combinations thereof on the at least one enzyme immobilized within at least one polyelectrolyte; and
- (c) polymerizing the end-capping agent.

2. The method of claim 1 additionally comprising immobilizing metal chelated catalytic particles within said at least one polyelectrolyte wherein said metal chelated catalytic particles are selected from the group consisting of metal chelated (EDA-$Cu^{2+}$) polymer, silica particles, and combinations thereof.

3. The method of claim 2 additionally comprising immobilizing adsorbent particles within said at least one polyelectrolyte.

4. The method of claim 3 wherein said adsorbent particles are functional catalytic particles made by incorporating quaternary ammonium surfactant to silica microparticles.

5. The method of claim 4, wherein said at least one polyelectrolyte is selected from the group consisting of branched or linear polyethyleneimine (PEI), polyacrylic acid (PAA), polystyrene sulfonate (PSS), polydiallyl dimethyl ammonium chloride (PDDA), and combinations thereof.

6. The method of claim 1 wherein the at least one enzyme is selected from the group consisting of organophosphorous hydrolase (OPH), organophosphorous acid anhydrolase (OPAA), DFPase, phosphotriesterases, and combinations thereof.

7. A method of making a bioactive catalytic material comprising the steps of:
- (a) immobilizing at least one enzyme within at least one polyelectrolyte;
- (b) depositing an end-capping agent on the at least one enzyme immobilized within at least one polyclectrolyte;
- (c) polymerizing the end-capping agent; and
- (d) immobilizing an adsorbent particle within said at least one polyclectrolyte.

8. The method of claim 7 additionally comprising immobilizing a metal chelated catalytic particle within said at least one polyelectrolyte wherein said metal chelated catalytic particle is selected from the group consisting of metal chelated (EDA-$Cu^{2+}$) polymer, silica particles, and combinations thereof.

9. The method of claim 7 wherein said adsorbent particle is a functional catalytic particle made by incorporating quaternary ammonium surfactant to silica microparticles.

10. The method of claim 7 wherein the at least one enzyme is selected from the group consisting of organophosphorous hydrolase (OPH), organophosphorous acid anhydrolase (OPAA), DFPase, phosphotriesterases, and combinations thereof.

11. The method of claim 7 wherein said at least one polyelectrolyte is selected from the group consisting of branched or linear polyethyleneimine (PEI), polyacrylic acid (PAA), polystyrene sulfonate (PSS), polydiallyl dimethyl ammonium chloride (PDDA), and combinations thereof.

12. The method of claim 7 wherein said end-capping agent is selected from the group consisting of 1,2-dihydroxypropyl methacrylate (DHPM), 1,2-dihydroxypropyl 4-vinylbenzyl ether (DHPVB), N-[3-trimethoxysilyl)propyl] ethylenediamine (TMSED), and combinations thereof.

13. The method of claim 12 wherein said at least one polyelectrolyte is selected from the group consisting of phosphonate, sulfonate, carboxylate, sulfate, phosphate, alkylamine, alkylammonium, quaternary pyridinium, pyridinium, and combinations thereof.

14. A method of making a bioactive catalytic material comprising the steps of:
- (a) immobilizing at least one enzyme within at least one polyclectrolyte;
- (b) depositing an end-capping agent selected from the group consisting of 1,2-dihydroxypropyl methacrylate (DHPM), 1,2-dihydroxypropyl 4-vinylbenzyl ether (DHPVB), N-[3-trimethoxysilyl)propyl]ethylenediamine (TMSED), and combinations thereof on the at least one enzyme immobilized within at least one polyelectrolyte;

(c) immobilizing a metal chelated catalytic particle within said at least one polyelectrolyte wherein said metal chelated catalytic particle is selected from the group consisting of metal chelated (EDA-$Cu^{2+}$) polymer, silica particles, and combinations thereof; and (d) polymerizing the end-capping agent.

15. The method of claim 12 additionally comprising immobilizing adsorbent particles within said at least one polyelectrolyte.

16. The method of claim 13 wherein said adsorbent particle is a functional catalytic particle made by incorporating quaternary ammonium surfactant to silica microparticles.

17. The method of claim 14 wherein said at least one polyelectrolyte is selected from the group consisting of branched or linear polyethyleneimine (PEI), polyacrylic acid (PAA), polystyrene sulfonate (PSS), polydiallyl dimethyl ammonium chloride (PDDA), phosphonate, sulfonate, carboxylate, sulfate, phosphate, alkylamine, alkylammonium, quaternary pyridinium, pyridinium, and combinations thereof.

18. The method of claim 12 wherein the at least one enzyme is selected from the group consisting of organophosphorous hydrolase (OPH), organophosphorous acid anhydrolase (OPAA), DFPase, phosphotriesterases, and combinations thereof.

* * * * *